(12) United States Patent
Osawa et al.

(10) Patent No.: US 8,136,899 B2
(45) Date of Patent: Mar. 20, 2012

(54) RACK DEVICE AND INCUBATOR HAVING THE SAME

(75) Inventors: Shinji Osawa, Funabashi (JP); Hiroki Busujima, Ota (JP)

(73) Assignee: Sanyo Electric Co., Ltd., Moriguchi-Shi (JP)

( * ) Notice: Subject to any disclaimer, the term of this patent is extended or adjusted under 35 U.S.C. 154(b) by 323 days.

(21) Appl. No.: 12/307,010

(22) PCT Filed: Jul. 3, 2007

(86) PCT No.: PCT/JP2007/063269
§ 371 (c)(1),
(2), (4) Date: Mar. 3, 2009

(87) PCT Pub. No.: WO2008/004533
PCT Pub. Date: Jan. 10, 2008

(65) Prior Publication Data
US 2009/0195129 A1    Aug. 6, 2009

(30) Foreign Application Priority Data
Jul. 5, 2006   (JP) ................................. 2006-185265

(51) Int. Cl.
*A47B 96/04*   (2006.01)
(52) U.S. Cl. ......... 312/408; 312/209; 211/103; 211/192
(58) Field of Classification Search ................. 312/209,
312/408, 351; 108/107, 147.16, 110, 109,
108/106; 211/103, 207, 192, 187, 190, 191;
248/244, 239, 222.41, 223.21, 220.21, 220.31,
248/220.43, 225.21, 250
See application file for complete search history.

(56) References Cited

U.S. PATENT DOCUMENTS

| | | | | | |
|---|---|---|---|---|---|
| 1,896,307 | A | * | 2/1933 | Hatch | 312/408 |
| 3,844,416 | A | * | 10/1974 | Potter | 211/162 |
| 4,138,019 | A | * | 2/1979 | Smith | 211/87.01 |

(Continued)

FOREIGN PATENT DOCUMENTS

JP   49-8964   3/1974
(Continued)

OTHER PUBLICATIONS

International Search Report for International Application No. PCT/JP2007/063269 dated Oct. 9, 2007.
Japanese Office Action mailed Sep. 13, 2011, with English Translation, in counterpart application JP 2006-185265.

*Primary Examiner* — Darnell Jayne
*Assistant Examiner* — Andres F Gallego
(74) *Attorney, Agent, or Firm* — Kratz, Quintos & Hanson, LLP

(57) ABSTRACT

A rack device having a receiver that can be prevented from being separated from a rack post in an incubator. A rack device in which a receiver is mounted between a pair of rack posts to hold a rack on the receiver includes a pair of engaging hooks which are formed in the receiver and a plurality of engaging holes which are formed in both the rack posts and in which both of the engaging hooks of the receiver disengageably engage, respectively. The rack posts are configured to be able to change an interval there between and select a first state in which the engaging hooks can be disengaged from the engaging holes and a second state in which the movement of the receiver is restricted while the engaging hooks be kept to engage in the engaging holes by changing the interval between the rack posts.

6 Claims, 9 Drawing Sheets

U.S. PATENT DOCUMENTS

| | | | |
|---|---|---|---|
| 4,212,445 A * | 7/1980 | Hagen | 248/245 |
| 4,681,381 A * | 7/1987 | Sevey | 312/333 |
| 5,305,898 A * | 4/1994 | Merl | 211/87.01 |
| 5,470,143 A * | 11/1995 | Gill | 312/334.4 |
| 5,483,902 A * | 1/1996 | Grosch | 108/143 |
| 5,895,020 A * | 4/1999 | Danzyger et al. | 248/295.11 |
| 5,950,974 A * | 9/1999 | Hoffmann | 248/223.41 |
| 6,675,946 B2 * | 1/2004 | Lutz | 193/35 TE |
| 2005/0084420 A1 * | 4/2005 | Osawa et al. | 422/99 |

FOREIGN PATENT DOCUMENTS

| | | |
|---|---|---|
| JP | 54-45721 | 3/1979 |
| JP | 3-25599 | 6/1991 |
| JP | 4-27844 | 7/1992 |
| JP | 2000-166536 | 6/2000 |
| JP | 2003-275068 A1 | 9/2003 |

* cited by examiner

RACK DEVICE AND INCUBATOR HAVING THE SAME

BACKGROUND OF THE INVENTION

The present invention relates to a rack device having a receiver mounted between a pair of rack posts to hold and support a rack on the receiver, and an incubator including the rack device.

Incubators for culturing cells or microbes (cultures) form a temperature/humidity/gas environment suitable for culturing the cultures in a culturing chamber. In the culturing chamber opened at the front, a rack device is provided to place a plurality of containers (Petri dishes and the like) accommodating the cultures (for example, see Japanese Patent Application Laid-Open No. 2000-166536).

In this case, the rack device includes pairs of front and rear rack posts which are fixed to right and left side walls of the culturing chamber, respectively, a pair of right and left receivers which are mounted between the front and rear rack posts on both of the side walls, respectively, and a rack which is held between both of the receivers. In this case, the receivers are provided with a lower wall and an upper wall arranged above the lower wall with an interval therebetween, and both right and left ends of the rack are inserted from the front between the lower and upper walls of both of the receivers to stably receive and hold the rack.

However, since a height of the rack should be changeable at need, the rack is fixed by engaging front and rear engaging hooks formed in the receivers with a plurality of engaging holes formed in a vertical direction in the front and rear rack posts. Accordingly, when the rack is removed from the culturing chamber, the engaging hooks are disengaged from the engaging holes just by, for example, a small amount of inclination for lifting the front side and thus an accident that the receivers are separated off occurs often.

SUMMARY OF THE INVENTION

The invention is contrived to solve the related conventional technical problem and provides a rack device having a receiver which can be surely prevented from being separated off from a rack post and an incubator including the rack device.

A rack device according to a first aspect of the invention is a rack device having a receiver mounted between a pair of rack posts to hold a rack on the receiver. The rack device includes a pair of engaging hooks which are formed in the receiver and a plurality of engaging holes which are formed in both of the rack posts and in which both of the engaging hooks of the receiver disengageably engage, respectively. The rack posts are configured to be able to change an interval therebetween and select a first state in which the engaging hooks can be disengaged from the engaging holes and a second state in which a movement of the receiver is restricted while the engaging hooks are kept to engage with the engaging holes by changing the interval between the rack posts.

In the rack device according to a second aspect of the invention, the receiver has a lower wall and an upper wall which are opposed to each other in a vertical direction, and the rack is held by being inserted between the lower wall and the upper wall.

The rack device according to a third aspect of the invention further includes a stopper capable of preventing the interval between both of the rack posts from being changed in the second state.

An incubator according to a fourth aspect of the invention, which includes a culturing chamber and forms an environment suitable for culturing a culture in the culturing chamber includes the rack device according to any one of the first to third aspects in the culturing chamber.

According to the invention, a rack device having a receiver mounted between a pair of rack posts to hold a rack on the receiver includes a pair of engaging hooks which are formed in the receiver and a plurality of engaging holes which are formed in both the rack posts and with which both the engaging hooks of the receiver disengageably engage, respectively, and the rack posts are configured to be able to change an interval therebetween and select a first state in which the engaging hooks can be disengaged from the engaging holes and a second state in which a movement of the receiver is restricted while the engaging hooks are kept to engage with the engaging holes by changing the interval between the rack posts. Accordingly, when a height of the rack is changed, the state of the rack posts is adjusted to the first state to disengage the engaging hooks of the receiver from the engaging holes of the rack posts and change a position of the receiver with respect to the rack posts. In this manner, the height of the rack can be arbitrarily changed.

Further, when the engaging hooks of the receiver are engaged with any engaging hole of the rack posts and the position is decided in this state, only by changing the interval between the rack posts and setting the second state, the movement of the receiver is restricted while the engaging hooks of the receiver are kept to engage with the engaging holes of the rack posts. Accordingly, a disadvantage in that, when the rack is held on the receiver or removed therefrom, the engagement between the engaging hooks and the engaging holes is released and the receiver is separated off can be surely prevented from occurring.

Particularly, as described in the second aspect, when the receiver has a lower wall and an upper wall which are opposed to each other in a vertical direction and the rack is held by being inserted between the lower wall and the upper wall, a force when the rack is operated is easily added to the receiver and the invention is very effective.

Further, as described in the third aspect, when a stopper is provided for preventing the interval between both the rack posts from being changed in the second state, such a disadvantage that the interval between the rack posts is changed by an error can be prevented from occurring.

In addition, when the rack device is used in a culturing chamber of an incubator forming an environment suitable for culturing a culture in the culturing chamber, a disadvantage in that, by the separation of the receiver, the important culture and/or containers might be damaged and the culturing chamber is contaminated can be prevented from occurring and the stable and safe culturing operation is very effectively performed.

DETAILED DESCRIPTION OF THE PREFERRED EMBODIMENTS

Figure 1:
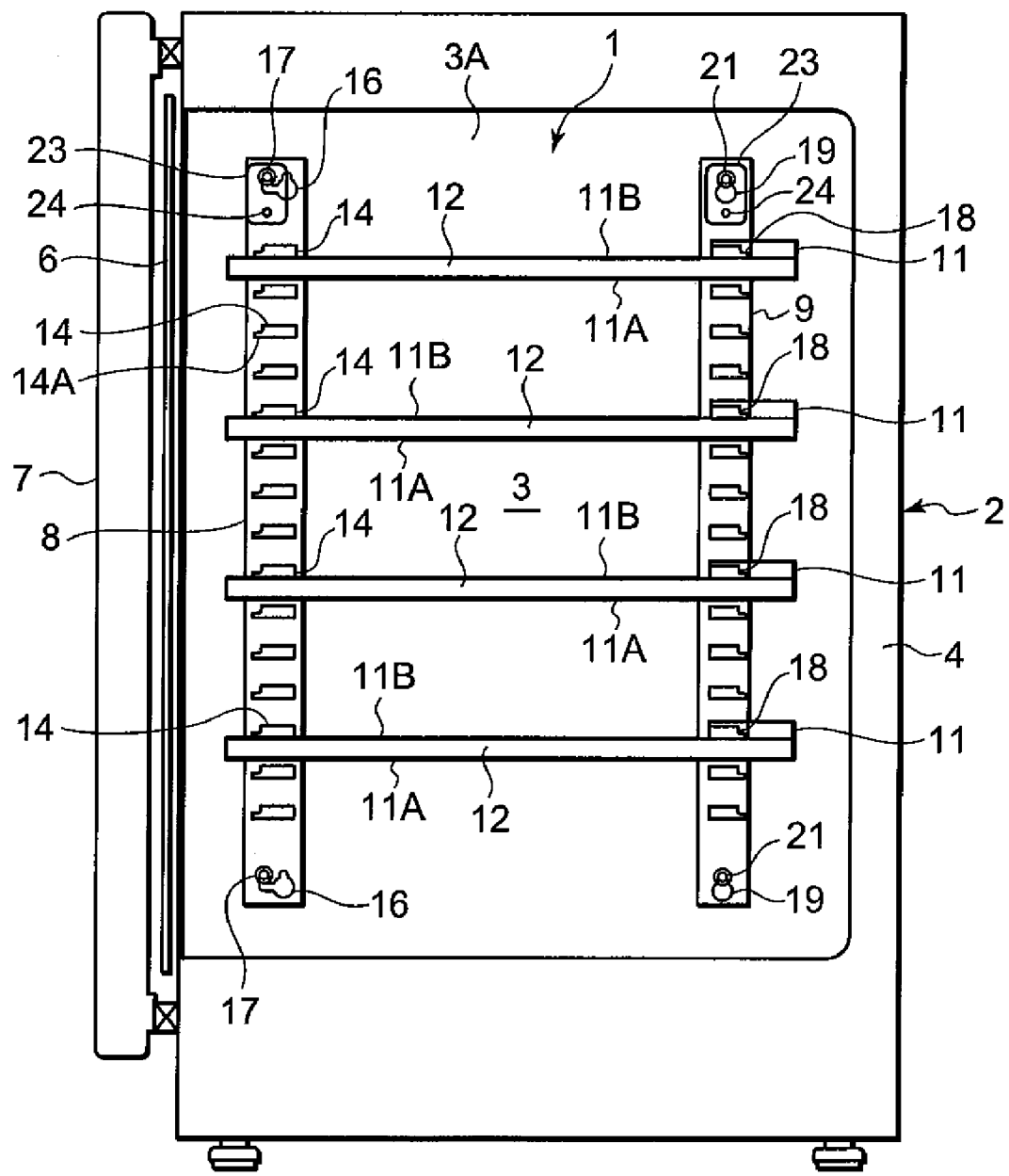
FIG. 1 is a schematic longitudinal sectional side view of an incubator according to an embodiment to which a rack device according to the invention is applied.
Figure 2:
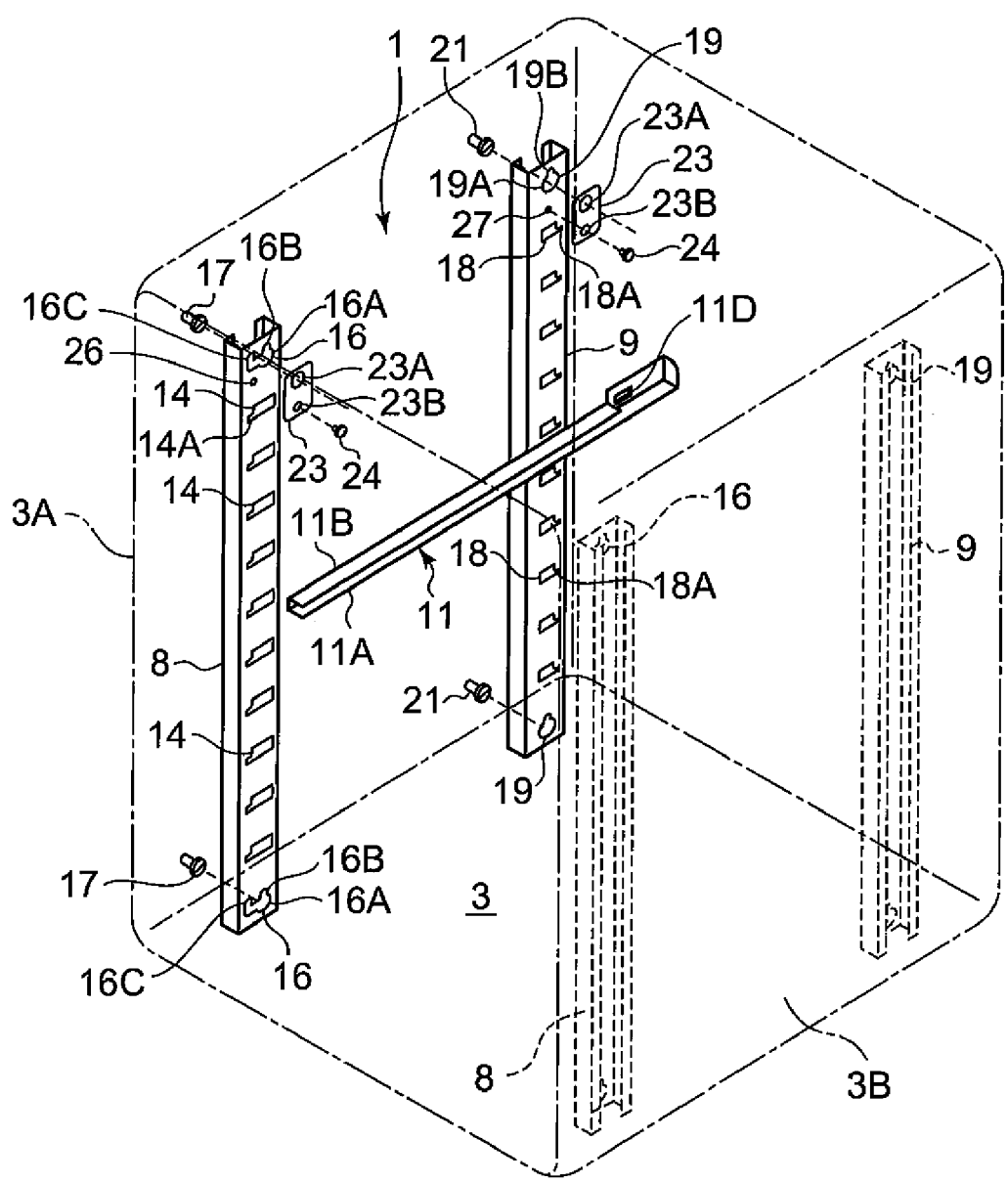
FIG. 2 is a perspective view of the inside of a culturing chamber of the incubator from which the rack device according to the invention is disassembled.
Figure 3:
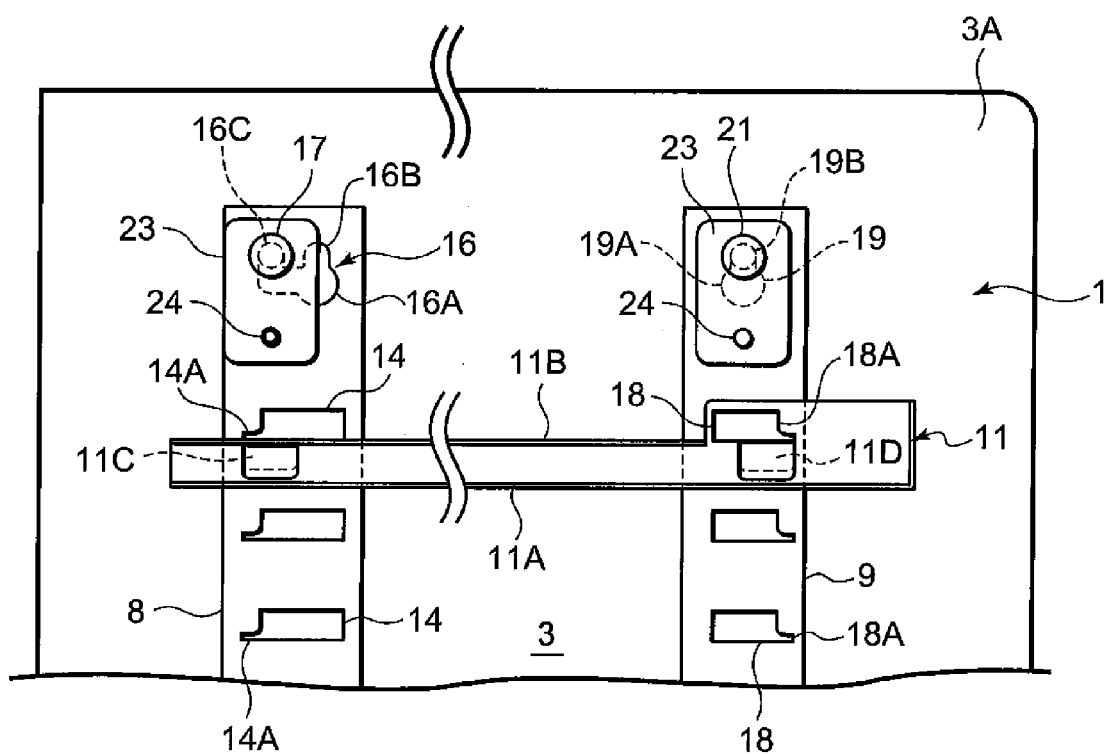
FIG. 3 is an enlarged view illustrating the rack device according to the invention (second state)
Figure 4:
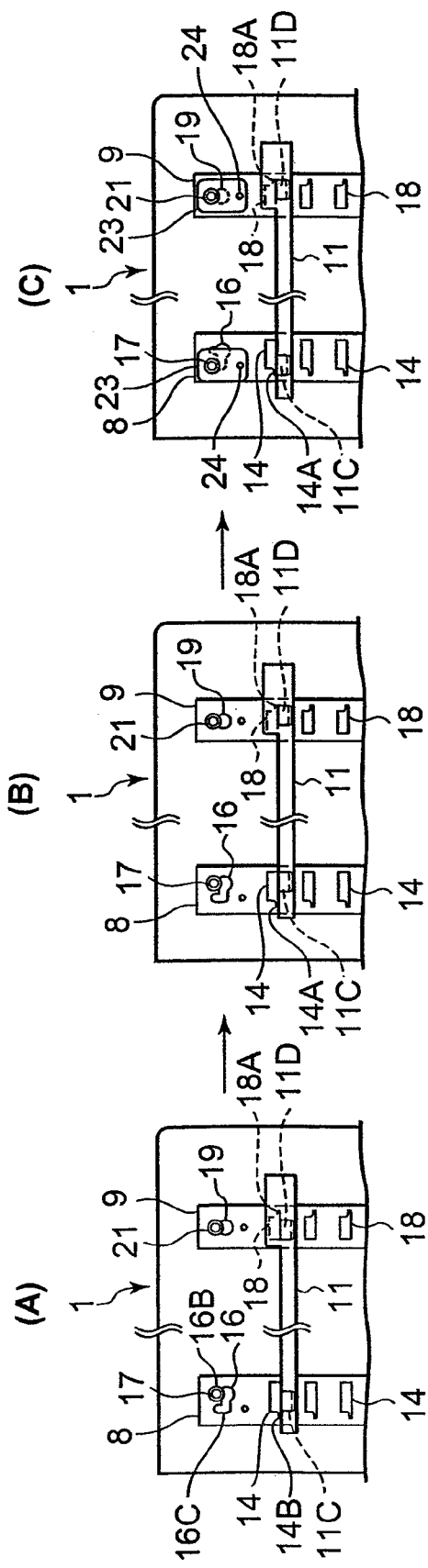
FIGS. 4(A) to 4(C) are diagrams illustrating a sequence of interval change between rack posts of the rack device according to the invention.

Next, an embodiment of the invention will be described based on the drawings. FIG. 1 is a schematic longitudinal sectional side view of an incubator 2 according to the embodiment to which a rack device 1 according to the invention is applied, FIG. 2 is a perspective view of the inside of a culturing chamber 3 of the incubator 2 from which the rack device 1 according to the invention is disassembled, and FIG. 3 is an enlarged view illustrating the rack device 1 according to the invention.

The incubator 2 according to the embodiment to which the invention is applied has a heat insulating container box 4, the culturing chamber 3 constituted in the heat insulating container box 4 and having an opened front surface, and openable interior and exterior doors 6 and 7 for closing the front surface opening of the culturing chamber 3. In the culturing chamber 3, a predetermined temperature (about +37° C.) and humidity (high humidity of 90% or more) suitable for culturing cultures such as cells or microbes are adjusted by a heater and a humidification device (not shown) and amounts of gas such as nitrogen, oxygen and carbon dioxide supplied to the culturing chamber 3 are adjusted to set a predetermined gas concentration suitable for culturing the cultures.

Each pair of rack posts 8 and 9 extending in a vertical direction are fixed back and forth to inner surfaces of right and left side walls 3A and 3B (fixing walls) of the culturing chamber 3, respectively. The rack posts 8 and 9 have a substantially U-shaped plane cross section. In addition, front right and left rack posts 8, 8 are opposed to each other and symmetrical with respect to a central surface in a horizontal direction of the culturing chamber 3, and rear right and left rack posts 9, 9 are also opposed to each other and symmetrical with respect to the central surface in the horizontal direction of the culturing chamber 3. Accordingly, in the description of the drawings other than FIG. 2, the rack posts 8 and 9 of the left side wall 3A of the culturing chamber 3 are used for the description.

Receivers 11 extending back and forth are fixed across the rack posts 8 and 9 of the side walls 3A and 3B, respectively, and right and left edges of a rack 12 are held on the right and left receivers 11, 11. These rack 12, receivers 11, 11, and rack posts 8, 9 and rack posts 8, 9 are made of metal such as stainless and constitute the rack device 1 according to the invention.

In this case, since the right and left receivers 11 are also symmetrical with respect to the central surface in the horizontal direction of the culturing chamber 3, the following description will be made using the receiver 11 mounted across the rack posts 8 and 9 of the left side wall 3A of the culturing chamber 3. In the receiver 11, rail-shaped lower wall 11A and upper wall 11B are formed and the space therebetween is opened to the front and rear and toward the inside of the culturing chamber 3. The right and left edges of the rack 12 are inserted from the front between the lower and upper walls 11A and 11B of the receivers 11, 11 so as to be slidably placed on the lower walls 11A, respectively. The upper walls 11B are slidably brought into contact with or closely disposed to an upper surface of the rack 12. In this manner, the rack 12 is stably held between the lower and upper walls 11A and 11B of the receivers 11, 11. Therefore, when being mounted or removed, the rack 12 is put in or taken out between the lower walls 11A and the upper walls 11B of the receivers 11 from the front.

Engaging hooks 11C and 11D are cut upward in the front and rear of a surface of the receiver 11 on the side of the side wall 3A (in case of the opposite right receiver 11, surface on the side of the side wall 3B). The engaging hooks 11C and 11D have a shape protruding to the side wall 3A by a predetermined dimension (thickness dimensions of the rack posts 8 and 9+clearance) and then curved downward and dropped.

Meanwhile, on a surface of the front rack post 8, which is disposed away from the side wall 3A (surface on the side of the opposite rack post 8), a plurality of engaging holes 14 . . . are formed in the vertical direction and fixing holes 16, 16 are formed at the upper and lower ends. As shown in FIGS. 2 and 3, the engaging holes 14 have a large rectangular shape having a width slightly larger than that of the engaging hook 11C (one engaging hook) as a whole, and from the bottom thereof, a slit 14A (engaging groove) further extending toward (direction separating from the rear (the other) rack post 9) by a predetermined dimension is formed.

The upper and lower fixing holes 16, 16 have a large diameter portion 16A through which a head of fixing screws (fixing portion) 17 fixed on the upper and lower sides of the front portion of the side wall 3A (in case of the opposite right rack post 8, side wall 3B) can pass, a first engaging portion 16B which continuously extends upward from the large diameter portion 16A and through which the head of the fixing screw 17 cannot pass, and a second engaging portion 16C which continuously extends forward (direction separating from the rear (the other) rack post 9) from the large diameter portion 16A by a predetermined distance and then is curved upward and through which the head of the fixing screw 17 cannot pass.

On a surface of the rear rack post 9, which is disposed away from the side wall 3A (surface on the side of the opposite rack post 9), a plurality of engaging holes 18 . . . are formed in the vertical direction and fixing holes 19, 19 are formed at the upper and lower ends. As shown in FIGS. 2 and 3, the engaging holes 18 have a large rectangular shape having a width slightly larger than that of the engaging hook 11D (the other engaging hook) as a whole, and from the bottom thereof, a slit 18A (engaging groove) further extending backward (direction separating from the front (one) rack post 8) by a predetermined dimension is formed.

The upper and lower fixing holes 19, 19 have a large diameter portion 19A through which a head of fixing screws (fixing portion) 21 fixed on the upper and lower sides of the rear portion of the side wall 3A (in case of the opposite right rack post 8, side wall 3B) can pass, and an engaging portion 19B which continuously extends upward from the large diameter portion 19A and through which the head of the fixing screw 21 cannot pass.

The reference number 23 in the drawings is a stopper composed of a rectangular stainless plate and the stopper has a positioning hole 23A which has a large diameter so as to pass the heads of the fixing screws 17 and 21 therethrough and a screw hole 23B which is formed below the positioning hole and into which a decorative screw (screw which can be operated by finger) 24 is inserted. Further, screw holes 26 and 27 to which the decorative screw 24 is screwed are formed below the second engaging portion 16C of the fixing hole 16 at the upper end of the rack post 8 and the large diameter portion 19A of the fixing hole 19 at the upper end of the rack post 9.

Next, with the above-described configuration, an assembling sequence of the rack device 1 according to the invention will be described with reference to FIGS. 4 to 9. First, the rear rack posts 9, 9 are fixed in the culturing chamber 3. In this case, first, the heads of the upper and lower fixing screws 21, 21 pass through the large diameter portions 19A of the upper and lower fixing holes 19, 19 of the rack post 9, respectively, and then are drawn down (automatically dropped) to engage the fixing screws 21, 21 with the engaging portions 19B of the upper and lower fixing holes 19, 19, respectively. Subsequently, the stopper 23 is put on the upper fixing hole 19 so as to pass the head of the upper fixing screw 21 through the positioning hole 23A thereof. In this state, the screw hole 23B is coincident with the screw hole 27. Finally, the decorative screw 24 is inserted into the screw hole 23B to be screwed to the screw hole 27 and thus the stopper 23 is fixed to the rack post 9.

In this state, even when the rack post 9 is to be moved upward, the upper fixing screw 21 is hooked by an edge of the positioning hole 23A of the stopper 23 and thus the rack post cannot move. Accordingly, the fixing screws 21, 21 are not separated from the engaging portions 19B of the fixing holes 19, 19 of the rack post 9. Thus, the rack posts 9 are stably fixed to the inner surfaces of the side walls 3A and 3B, respectively.

Figure 5:
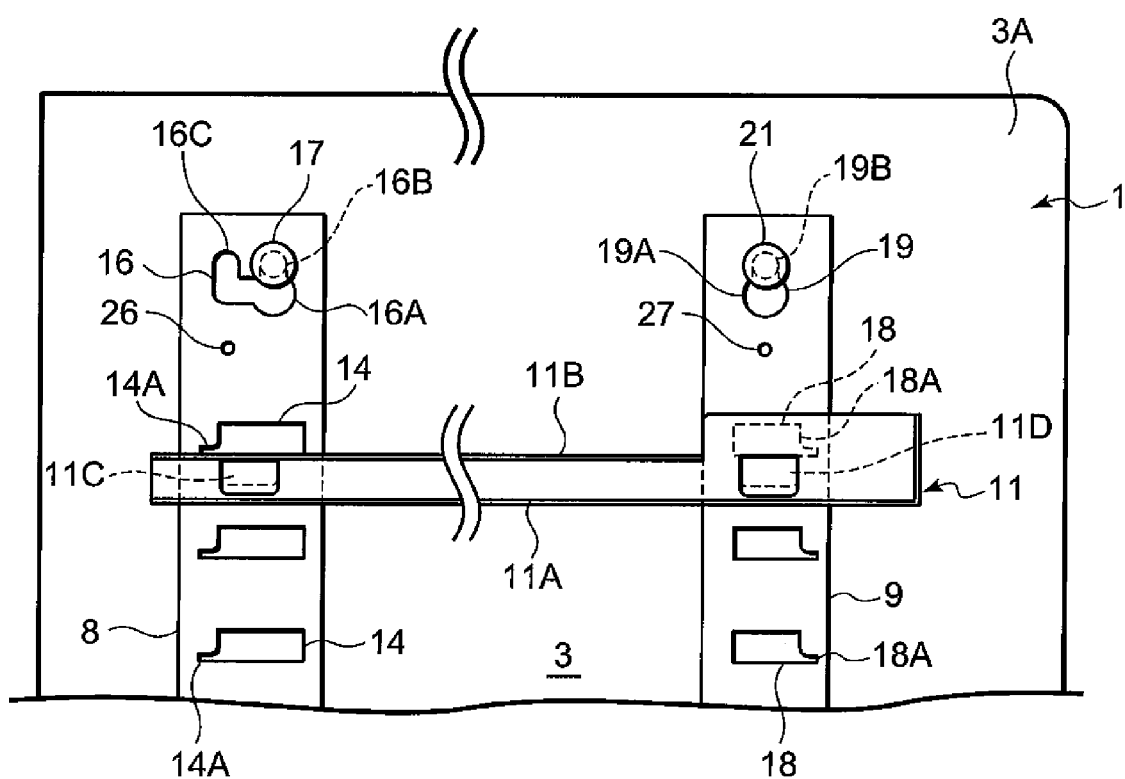
FIG. 5 is an enlarged view when the rack posts of the rack device according to the invention are in a first state.
Figure 6:
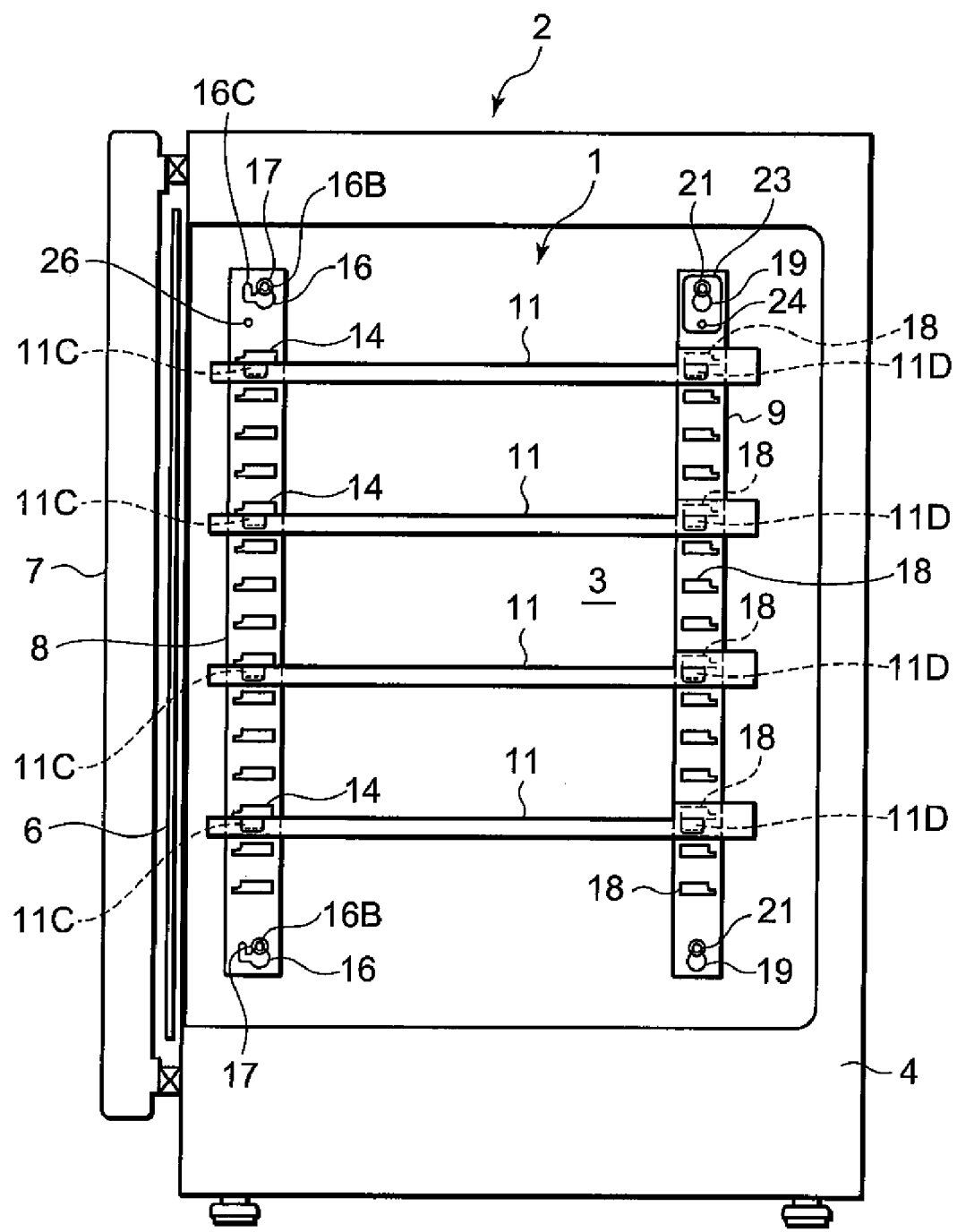
FIG. 6 is a schematic longitudinal sectional side view of the incubator when the rack device according to the invention is in a state of FIG. 5.
Figure 7:
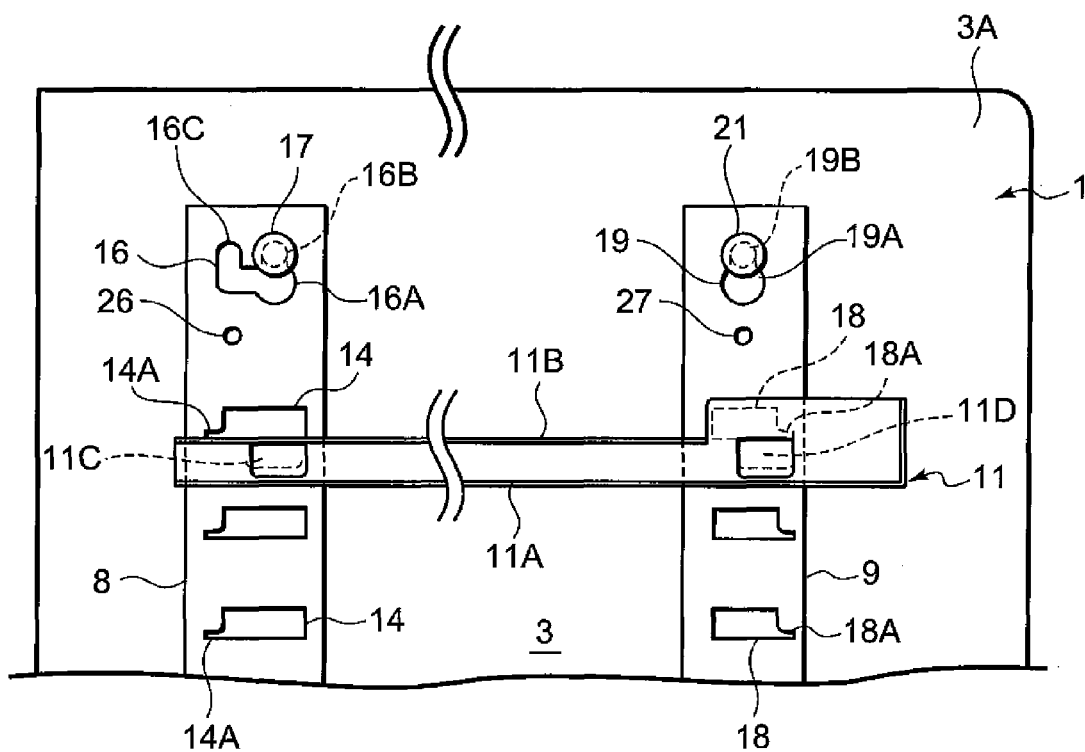
FIG. 7 is another enlarged view when the rack posts of the rack device according to the invention are in a first state.
Figure 8:
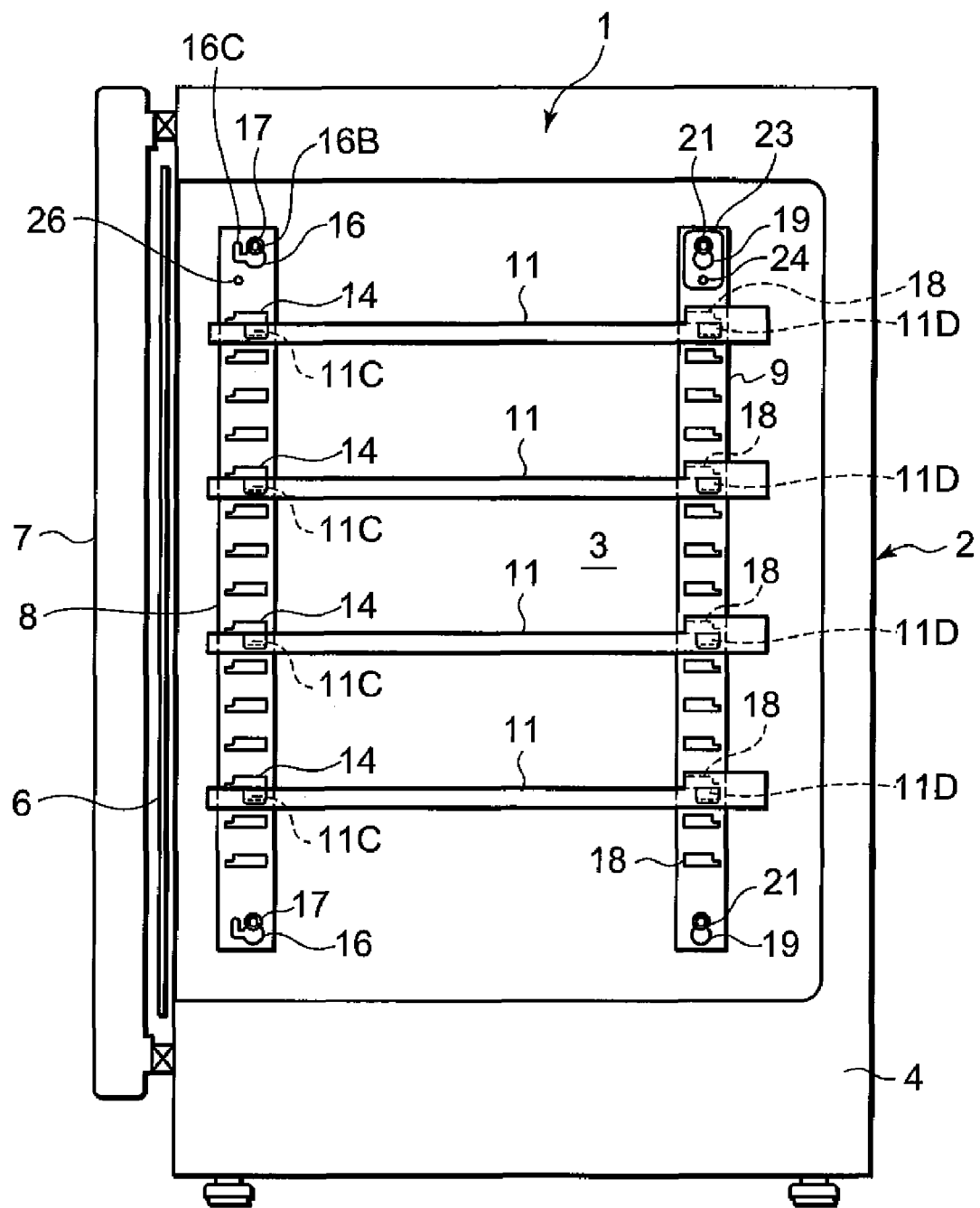
FIG. 8 is a schematic longitudinal sectional side view of the incubator when the rack device according to the invention is in a state of FIG. 7.
Figure 9:
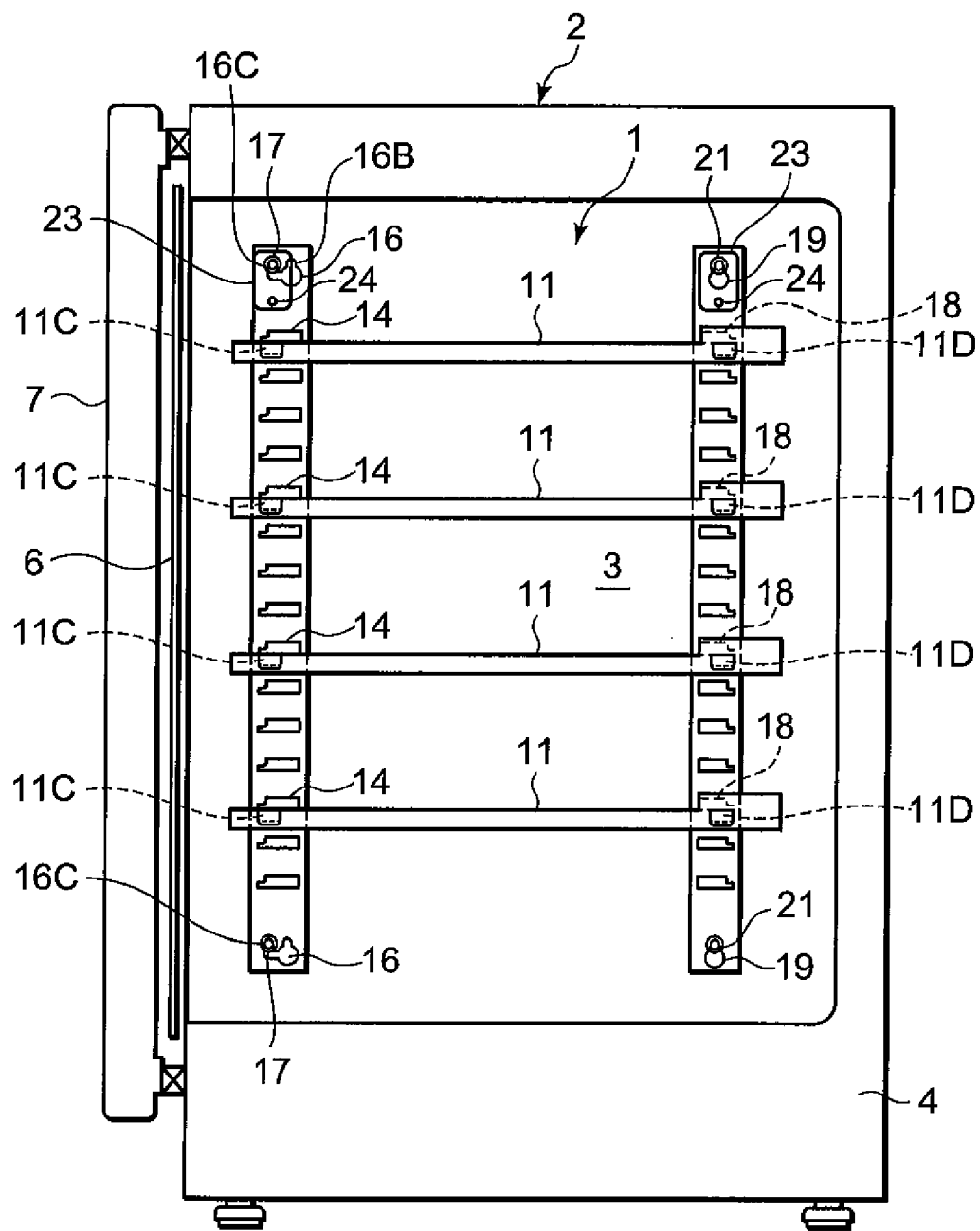
FIG. 9 is a schematic longitudinal sectional side view of the incubator when the rack device according to the invention is in a state of FIG. 3.

Then, the front rack posts 8, 8 are fixed in the culturing chamber 3. In this case, first, the heads of the upper and lower fixing screws 17, 17 pass through the large diameter portions 16A of the upper and lower fixing holes 16, 16 of the rack post 8, respectively, and then are drawn down (automatically dropped) to engage the fixing screws 17, 17 with the first engaging portions 16B of the upper and lower fixing holes 16, 16, respectively. This state is shown in FIG. 4(A) and FIGS. 5 and 6 (first state).

In this first state in which the fixing screws 17 engage with the first engaging portions 16B of the fixing holes 16, respectively, the front rack post 8 is separated from the rear rack post 9 and thus the interval between both the rack posts 8 and 9 increases. In the embodiment, the dimension between an inlet (rear end) of the slit 14A of the engaging hole 14 of the rack post 8 and an inlet (front end) of the slit 18A of the engaging hole 18 of the rack post 9 is set so as to be larger than a dimension from the front end of the front engaging hook 11C of the receiver 11 to the rear end of the rear engaging hook 11D.

In this state, a height position of the rack 12 is determined and the engaging holes 14 and 18 at the above height are selected to mount the receiver 11 across the front and rear rack posts 8 and 9. In this first state, when the rear engaging hook 11D of the receiver 11 is allowed to correspond to a wide portion of the engaging hole 18 in front of the slit 18A, the front engaging hook 11C corresponds to a wide portion of the rear engaging hole 14 behind the slit 14A. Accordingly, both the engaging hooks 11C and 11D can be disengageably engaged with the engaging holes 14 and 18 of the rack posts 8 and 9 (FIGS. 5 and 6).

Next, when the receiver 11 is moved backward (direction of the other rack post 9), the rear engaging hook 11D enter the slit 18A of the engaging hole 18 of the rack post 9 and engages therewith. In this state, the vertical and backward movement of the engaging hook 11D is disturbed (FIG. 4(B), and FIGS. 7 and 8).

Next, the front rack post 8 is lifted to separate the fixing screw 17 from the first engaging portion 16B. In this state, the rack post 8 is moved to the rear (direction approaching the rack post 9). By this movement, the fixing screw 17 moves forward through the large diameter portion 16A of the fixing hole 16 and finally reaches the lower side of the second engaging portion 16C. When being drawn down (automatically dropped), the fixing screw 17 enters the second engaging portion 16C of the fixing hole 16 and engages therewith (second state). The rack device 1 according to the invention can select the first state and the second state of the rack posts 8 and 9 by a simple operation of the rack post 8.

In this second state, the interval between both the rack posts 8 and 9 is narrower than in the state of FIGS. 5 and 6.

In the embodiment, in the second state, a dimension between the innermost end (front end) of the slit 14A of the engaging hole 14 of the rack post 8 and the innermost end (rear end) of the slit 18A of the engaging hole 18 of the rack post 9 is set so as to be substantially coincident with a dimension from the front end of the front engaging hook 11C of the receiver 11 to the rear end of the rear engaging hook 11D. Accordingly, the front engaging hook 11C of the receiver 11 enters the slit 14A of the engaging hole 14 of the rack post 8 and engages therewith and thus the vertical and forward movement of the engaging hook 11C is disturbed (FIG. 4(C), and FIGS. 1, 3 and 9). In addition, the rear engaging hook 11D also enters the slit 18A simultaneously and thus the movement of the receiver 11 in any one of the vertical, front-back, and horizontal directions is restricted (prevented). Therefore, the engaging hooks 11C and 11D are not separated from the engaging holes 14 and 18.

Finally, the stopper 23 is put on the upper fixing hole 16 to pass the head of the upper fixing screw 17 through the positioning hole 23A thereof. In this state, the screw hole 23B is coincident with the screw hole 26. The decorative screw 24 is inserted into the screw hole 23B to be screwed to the screw hole 26, finally. In this manner, the stopper 23 is fixed to the rack post 8.

In this state, even when the rack post 8 is to be moved forward, the upper fixing screw 17 is hooked by an edge of the positioning hole 23A of the stopper 23 and thus cannot move. Thus, the fixing screws 17, 17 are not separated from the second engaging portions 16C of the fixing holes 16, 16 of the rack post 8. Accordingly, the rack posts 8 are stably fixed to the inner surfaces of the side walls 3A and 3B, respectively.

In this manner, the rack posts 8 and 9 are fixed and the receivers 11 are mounted and then the right and left edges of the rack 12 are inserted from the front between the lower walls 11A and the upper walls 11P of the right and left receivers 11, 11, respectively, to hold the rack 12. As a result, the rack device 1 is finished.

Herein, when a force for inclining is added to, for example, locate the front side to the upper side in order to pull the rack 12 out of the culturing chamber 3, a force in a direction in which the front side is lifted up is applied to the receiver 11 since the rack 12 is held between the lower wall 11A and the upper wall 11B of the receiver 11. However, in the invention, since the front and rear engaging hooks 11C and 11D of the receiver 11 stably engage with the engaging holes 14 and 18 of the rack posts 8 and 9 and are restricted so as not to move in any direction, the engaging hooks 11C and 11D are not separated from the engaging holes 14 and 18 in such a cases and the receiver 11 is not separated off. Accordingly, a disadvantage in that the dropped receiver 11 hits and damages the culturing containers (Petri dishes) placed on the lower rack 12, thereby damaging the important samples or contaminating the inside of the culturing chamber 3 is prevented from occurring.

Moreover, since the movement of the rack posts 8 and 9 is also disturbed by the stopper 23, the interval between both the rack posts 8 and 9 is prevented from being changed in the second state and thus a disadvantage in that the interval between the rack posts 8 and 9 is changed by mistake can be prevented from occurring.

Herein, when the height of the rack 12 is changed, the decorative screw 24 is loosened to separate the stopper 23 of the front rack post 8 and the rack post 8 is lifted up to separate the fixing screw 17 from the second engaging portion 16C of the fixing hole 16. Then, the rack post 8 is moved forward (direction separating from the rack post 9) to engage the fixing screw 17 with the first engaging portion 16B to thereby set the above-described first state. In this state, since the engaging hooks 11C and 11D of the receiver 11 can be disengaged from the engaging holes 14 and 18 of the rack posts 8 and 9, it is preferable that the receiver 11 is separated and engaged with the engaging holes 14 and 18 at a different height and then the interval between the rack posts 8 and 9 is reduced as described above to set the second state. In this manner, the height of the rack 12 can be arbitrarily and easily changed also.

In the embodiment, the rack device according to the invention is applied to the incubator. Nevertheless, it is to be appreciated that the invention is not limited to the incubator and is usefully applied to refrigerators, reservoirs, general cabinets and the like. In addition, in the embodiment, the second state is set by reducing the interval between the rack posts 8 and 9, but is not limited thereto and the second state may be set by increasing the interval. In this case, the slits 14A and 18A of the engaging holes 14 and 18 extend in a reverse direction with respect to that of the embodiment, respectively.

What is claimed is:

1. A rack device having a receiver mounted between a pair of rack posts to hold a rack on the receiver, the rack device comprising:
   a pair of engaging hooks which are formed in the receiver; and
   a plurality of engaging holes which are formed in both of the rack posts for permitting both of the engaging hooks of the receiver to disengageably engage therein, respectively;
   at least one of the rack posts has a fixing hole to allow a change in the interval therebetween, wherein when the rack posts are in a first state the engaging hooks on the receiver are disengageable from the engaging holes of the rack posts, and when in a second state, the receiver is prevented from disengagement from the rack posts while the engaging hooks are kept to engage in the engaging holes by changing the interval between the rack posts.

2. The rack device according to claim 1,
   wherein the receiver has a lower wall and an upper wall which are opposed to each other in a vertical direction, and the rack is held by being inserted between the lower wall and the upper wall.

3. The rack device according to claim 2, further comprising:
   a stopper for preventing the interval between both the rack posts from being changed in the second state.

4. An incubator including a culturing chamber and forming an environment suitable for culturing a culture in the culturing chamber, the incubator comprising:
   the rack device according to claim 3 in the culturing chamber.

5. An incubator including a culturing chamber and forming an environment suitable for culturing a culture in the culturing chamber, the incubator comprising:
   the rack device according to claim 2 in the culturing chamber.

6. An incubator including a culturing chamber and forming an environment suitable for culturing a culture in the culturing chamber, the incubator comprising:
   the rack device according to claim 1 in the culturing chamber.

* * * * *